United States Patent [19]
Crawford et al.

[11] Patent Number: 5,175,977
[45] Date of Patent: Jan. 5, 1993

[54] KIT AND METHOD FOR PACKAGING GLOVES

[75] Inventors: Mark A. Crawford, Sandy, Utah; T. Andrew Guhl, Oakville, Canada; J. Robert Stanley, West Jordan, Utah

[73] Assignee: Becton, Dickinson and Company, Franklin Lakes, N.J.

[21] Appl. No.: 799,223

[22] Filed: Nov. 27, 1991

Related U.S. Application Data

[62] Division of Ser. No. 681,213, Apr. 5, 1991, Pat. No. 5,117,981, which is a division of Ser. No. 249,272, Sep. 27, 1988, abandoned.

[51] Int. Cl.$^5$ .................. B65B 13/02; B65B 63/04
[52] U.S. Cl. ............................... 53/399; 53/410; 53/429; 53/430
[58] Field of Search .......... 53/116, 117, 118, 119, 53/120, 139.5, 399, 410, 415, 429, 430

[56] References Cited

U.S. PATENT DOCUMENTS

| | | | |
|---|---|---|---|
| 2,681,702 | 6/1954 | Kuenn et al. | 53/118 |
| 3,237,363 | 3/1966 | Spohr | 53/429 |
| 3,393,633 | 7/1968 | Hoffman et al. | 53/399 X |
| 4,094,120 | 6/1978 | Goncalves | 53/429 |
| 4,379,384 | 4/1983 | Nishikawa | 53/415 |
| 4,567,065 | 1/1986 | Schneiderman | 53/429 X |
| 4,950,511 | 8/1990 | Francis | 53/430 X |

Primary Examiner—John Sipos
Assistant Examiner—Linda B. Johnson
Attorney, Agent, or Firm—Arthur D. Dawson

[57] ABSTRACT

A kit comprises a tray with a well for a tourniquet, a dressing to use with a medical device inserted into a blood vessel. An antimicrobial treatment in the well disinfects an area of skin through which the medical device punctures the vessel. A pair of juxtaposed gloves with the finger ends, the hand parts and the cuff portions against one another are rolled up along their longitude from their fingers to their cuffs driving out air entrapped within the gloves. The process of rolling from the fingers to the cuffs leaves the cuffs of each glove at the periphery of the rolled generally cylindrical gloves for access to the inside of each when donning. A method for rolling gloves into a relatively cylindrical package, includes setting the gloves side by side with the finger ends, the hand parts, and the wrist or cuff portions juxtaposed. The finger portions are gathered into an axial bundle and rolled from the finger ends toward the palm or back hand parts driving out air within the gloves. Rolling along the elongate longitude of the gloves to the cuff or wrist portions, drives air from the cuffs and provides a cylindrical package. The method may include the added step of binding the rolled gloves with a band or tape. The compact package of gloves rolled up together along their longitude has binding about the middle to hold the rolled glove pair together so they are diametrically smaller than they are wide.

10 Claims, 2 Drawing Sheets

KIT AND METHOD FOR PACKAGING GLOVES

This is a division of application Ser. No. 07/681,213, filed Apr. 5, 1991 now U.S. Pat. No. 5,117,981, which is a division of Ser. No. 07/249,272 filed Sep. 27, 1988, now abandoned.

BACKGROUND OF THE INVENTION

1. Field of the Invention

This invention relates to a kit and method for packing gloves in a kit, and more specifically, to a kit and method for preparing a glove pair for a packaged kit which would not have gloves.

2. Background Description

Infection control is an important concern in the medical field in view of the possibility of life threatening illness or incurable disease transmission in the health care environment. Practitioners that have contact with the sick and with biohazardous material risk their lives on a daily basis. The entire field of health care has changed with respect to the great concern and precautions undertaken for preventing the spread of infection. There was a time when the use of gloves as an infection barrier was intended to prevent the surgeon from contaminating the patient. Today even dentists wear gloves while routinely examining their patients.

Because of the desire to limit transmission of infection to their patients during surgery, doctors have followed a scrub procedure before donning their surgical gloves. The procedures for donning surgical gloves has developed out of a recognized need to maintain the sterility of the exterior surface of the gloves so as to prevent transmission of infection to the patient. Surgeon's gloves are packaged so that they can be donned without contaminating the outside surface. In particular, the aseptic presentation of the pair of surgeon's gloves is part of the way such gloves are packed to aid in donning after the package containing the gloves is opened. The cuffs are folded up toward the hand portion so each glove can be handled by the inside surface while donning. The outside of the glove remains sterile since only the inside is touched with an ungloved hand. After one glove is on the second glove can be entered with the fingers of the ungloved hand and the gloved hand can be used to smooth the outside and to unfolded the cuff downwardly over the the wrist by touching only the outside surface of the glove. The glove package is designed to be opened without touching the outside of the gloves and so that the cuffs are folded as described.

The most commonly used latex gloves have been well known as surgeon's gloves because of their very thin finger tips which allow sensitivity to the doctor's sense of touch even with the gloves on the surgeon's hands. Latex gloves are designed to provide minimal impairment of the sense of feel and offer practically no restraint to the surgeon's dexterity during use. Gloves of other materials which are thicker, hypoallergenic or solvent resistant are available for specific uses. The packaging of the gloves for other uses is such that those gloves remain sterile during warehousing, shipment and before opening for use. The donning requirements are not as important in non surgical situations where the gloves primary purpose is to prevent the practitioner from becoming infected.

Frequently the health care specialist has to handle dangerous or possibly infectious specimens, contaminated bedding or used medical supplies, equipment or devices. There is no simple way of knowing if there is contamination and so the safest approach is to use gloves as a barrier or infection control. Biohazardous substancces are frequently handled and tested for deadly virus, infection or the like and those substances typically require special care during handling. Consequently, the need and desire for gloves has increased to an extent that those involved in health care use several pairs of gloves each workday.

Areas of considerable concern, since acquired immune deficiency syndrome has spread, are medical procedures where blood is handled. Similarly, herpes and hepatitis are also dangers which require the use of gloves. In order to protect himself, the practitioner must remember to find a clean glove pair before undertaking to perform a procedure which involves blood or other bodily fluids. The extreme demand for the protection afforded by gloves often makes them difficult to find and so the convenience of using gloves is frequently troublesome.

During the last twenty five years disposable medical devices have been used for a variety of medical treatment and procedures. Disposable medical devices have contributed largely to preventing the spread of infection by eliminating reuse of needles, blades, containers and the like. Even with sterilization the handling necessary to prepare reusable medical devices creates a risk of infection. To add to the convenience of disposable medical devices manufacturers have for some time packaged the items required for various procedures in a common tray. One such package has included an intravenous catheter, a dressing a tourniquet, a form of disinfectant or antimicrobial treatment and other required paraphernalia needed to effect a catheterization. That is not to suggest that there have not been other trays for other purposes because there have been as many types of assemblies as there are medical procedures.

The purchasers of supplies for the health care needs prefer to order specific trays since the allocation of the cost of individual components to a particular patient is practically impossible. With a specific tray comes all of the items in a neat convenient package and each tray is sterilized and sealed when manufactured. Moreover gloves have been included in trays arranged for numerous surgical procedures, the addition of gloves has typically included the package for aseptic presentation as already explained. The idea of gloves in a package designed to contain merely the pieces used to start an intravenous catheter would suggest that the tray be doubled in size to accommodate such gloves.

Heretofore, a simple way to prepare gloves for their addition to a kit arranged to start a catheter was not available and such a kit including gloves arranged to reside with the other components was simply unknown.

SUMMARY OF THE INVENTION

A kit for preparing and dressing an intravenous catheter site comprises a tray in the form of a blister pack having a recessed well to receive the components of the kit.

The blister pack includes a sealing flange about the well. In the well of a preferred embodiment is a tourniquet which may be added to the kit for use in aiding the location of a blood vessel for purposes of a medical procedure. A dressing including an adhesive member and an absorbent member is preferably added to the well for use in connection with the application of a medical device to the located blood vessel. Similarly, an antimicrobial treatment is in the well for use in disinfecting an area of skin through which the medical device is to be applied to the vessel. A cover may be added to the tray flange over the well for indicating the source and nature of the components within the kit.

The preferred kit has a glove pair of a thin non-porous, flexible resilient material. The gloves have been placed juxtaposed with the finger ends against one another, the hand part against one another and the cuff portions against one another. The juxtaposed gloves are preferably rolled up along their longitudinal elongate dimension as a pair from their fingers to their cuffs to drive out air entrapped within the gloves. The process of rolling from the fingers to the cuffs eliminates the air within the gloves leaving the cuffs of each glove at the periphery of the rolled generally cylindrical glove pair for ease in access to the inside of each glove during donning.

The preferred method for rolling a non-porous glove pair into a relatively cylindrical package, includes placing the glove pair in side by side juxtaposed relation with the finger ends of the respective gloves adjacent to one another, the palm or back hand parts of the respective gloves adjacent to one another, and the wrist or cuff portions of the respective gloves adjacent to one another. Gathering the finger portions of the adjacent gloves into a relatively axial bundle with respect to the elongate longitudinal dimension of the glove pair so the next step of rolling from the finger ends of the juxtaposed gloves toward the palm or back hand part is performed against a relatively flat and rigid surface to exclude air within the gloves by the pressure applied against the surface while rolling. The thumbs of the juxtaposed gloves are incorporated into the rolled bundle, and the glove pair rolling is continued along the elongate longitudinal dimension of the glove pair. By rolling toward the cuff or wrist portions, while bearing against the bundle remaining air is driven from the cuff ends of the gloves. The glove pair is rolled as a unit into a cylindrical package about the width of the gloves.

The preferred method may include the additional step of binding the rolled gloves with a fastener. The method of binding may preferably have an elastic band shaped member about the cylindrical package. The band shaped member may be expanded to fit over the rolled gloves and released to retain the rolled gloves. In an alternate approach the step of binding is accomplished by using a piece of pressure sensitive adhesive tape.

The method may preferably have the additional steps of adding a piece of innerwrap between the gloves of the pair of juxtaposed gloves and creating a sandwich for rolling into the cylindrical package. The method with the innerwrap may include the additional step of binding the rolled gloves with a fastener. The method of binding may have an elastic band shaped member. The band shaped member may be expanded to fit over the rolled gloves and released to retain the rolled gloves. In an alternate approach the step of binding is accomplished by using a piece of pressure sensitive adhesive tape.

A compact package has the glove pair placed juxtaposed to one another with finger ends against one another, a pair of hand parts against one another and a pair of cuff portions against one another. The glove pair is rolled up together along its longitudinal elongate dimension from the finger ends to the cuff portions, removing air entrapped within the gloves. A binding located about the middle of the rolled glove pair circumscribes and holds the rolled glove pair together. The compact package is such that the length of the unrolled glove pair is substantially greater than the the width and the rolled glove pair is diametrically less than the width thereof.

DETAILED DESCRIPTION OF THE DRAWINGS

Figure 1:
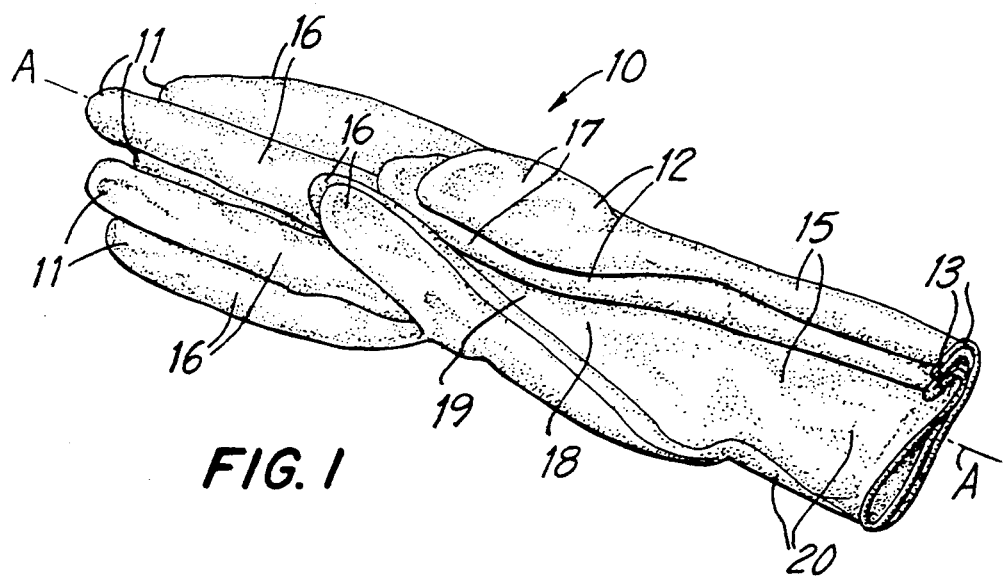
FIG. 1 is a perspective view of a pair of juxtaposed gloves prior to being rolled into the preferred form of a compact cylindrical package of the present invention.

While this invention is satisfied by embodiments in many different forms, there are shown in the drawings and will herein be described in detail a preferred embodiment and an alternate embodiment of the invention, with the understanding that the present disclosure is to be considered as exemplary of the principles of the invention and is not intended to limit the invention to the embodiments illustrated. The scope of the invention will be measured by the appended claims and their equivalents.

FIG. 1 is a perspective view of a glove pair 10 laid in juxtaposed position with a plurality of finger ends 11 adjacent to one another, a pair hand parts 12 adjacent to one another and a pair cuff portions 13 adjacent to one another. The glove pair 10 are positioned in this manner just prior to bring rolled in to a compact cylindrical package 14 or 14a (see FIGS. 4 and 5). The glove pair 10 of the invention may be made of a variety of non-porous materials including latex, vinyl, or other thin flexible material so as to offer protection when worn. Although not individually shown, each glove 15 in the glove pair 10 has five fingers 16 including the thumb 17, a palm or back 18 in its central section 19 and a cuff 20. In FIG. 1 the thumbs 17 of the glove pair 10 are placed up against the hand parts 12 of the glove pair 10 such that the glove pair 10 has an elongate longitudinal dimension from the fingers 16 to the cuff 20 as along line A—A which is approximately the center line of the glove pair 10. On each glove 15 the fingers 16 each include the finger ends 11, the palm or back 18 include a hand part 12 and the cuff 20 includes cuff portion 13.

Figure 2:
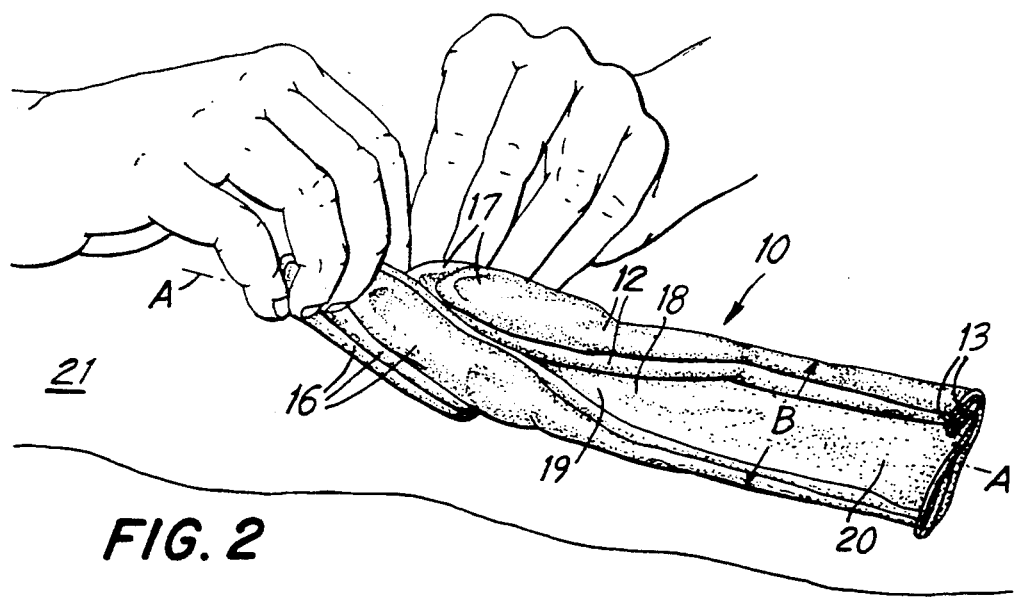
FIG. 2 is a showing of a step of gathering the fingers just prior to when the gloves are to be rolled from the finger ends to create the preferred form of the package of the present invention.

In FIG. 2 the process of rolling the glove pair 10 is shown at the beginning step wherein the finger ends 11 are first gathered. It may be seen that glove pair 10 are laid against a surface 21 and the finger ends 11 are gathered toward the longitudinal line A—A so that the glove pair 10 may be rolled from the finger ends 11 to the portions 13. During the rolling process, air which is in the glove pair 10 is caused to leave by means of the pressure applied. In particular, the person rolling the glove pair 10 presses the finger ends 11 against the surface 21 to drive any air therewithin toward the hand parts 12 of the glove pair 10. The glove pair 10 are maintained in a narrow assembly as depicted in FIG. 2 such that the width "B" is considerably less than the distance from the finger ends 11 to the cuff portions 13. The dexterity needed to gather and then roll the glove pair 10 is not great and a neat compact package 14 may quickly be made without practice, skill or effort.

Figure 3:
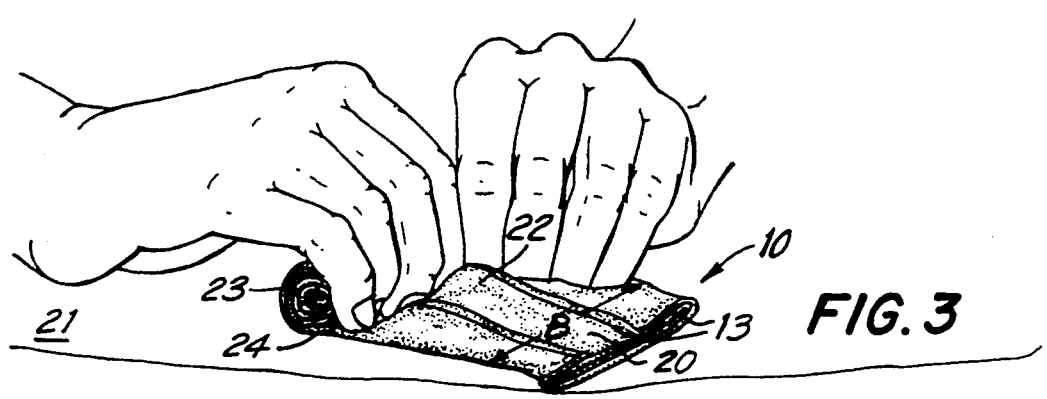
FIG. 3 is an illustration of the rolling method wherein the juxtaposed gloves are shown partially rolled to the hand parts of the gloves in the process of creating the preferred form of the package of the present invention.

FIG. 3 shows the result of the continued rolling of the glove pair 10 and more specifically, the glove pair 10 after they are rolled just past the hand parts 12. As is shown in FIG. 3 the air is driven toward the cuff portions 13 of the glove pair 10 during rolling. There is a slight bulge 22 located in advance of the rolled glove pair 10 which bulge 22 suggests the air within the glove pair 10 that is being forced toward the portions 13. Also illustrated in FIG. 3 is a partially rolled package 23 having the finger ends 11 and hand parts 12 kept tightly rolled and contained behind an area 24 of the advancing pressure whereat air within the glove pair 10 is driven outwardly of the glove pair 10. The width "B" is maintained narrow to keep the size of the resulting package 14 as compact as possible. Because the glove pair 10 are typically of thin non-porous material which is usually very flexible and elastic care is taken during the rolling process not to stretch or tear the glove pair 10.

Figure 4:
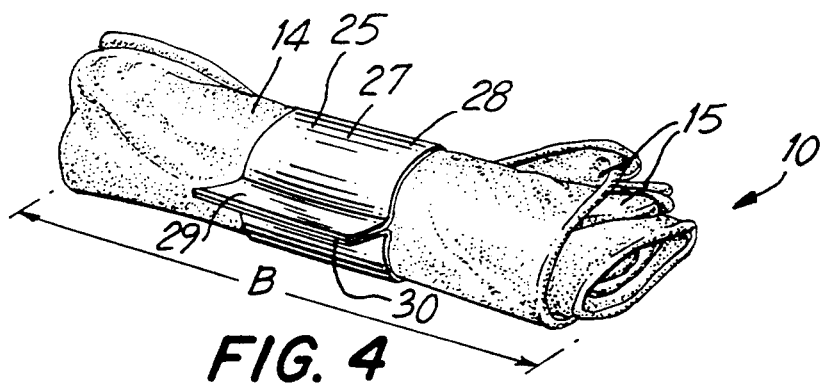
FIG. 4 is an enlarged perspective view of a preferred form of the binding of a pressure sensitive tape used to hold the compact rolled cylindrical package of the present invention.
Figure 5:
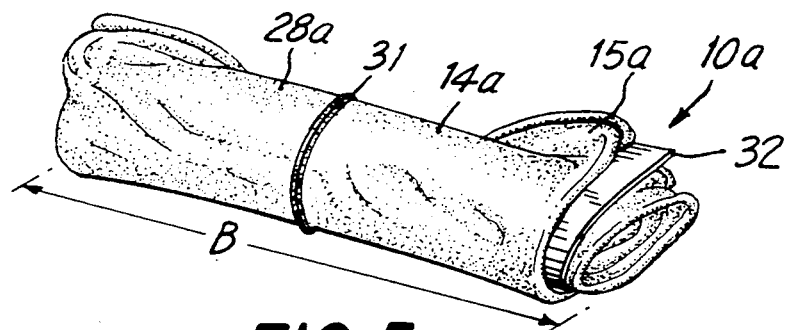
FIG. 5 is an enlarged perspective view of an alternate form of the binding of an elastic band used to hold the compact rolled cylindrical package of the present invention.

FIG. 4 is an enlarged perspective view of a preferred form of a binding 25 used to hold the rolled gloves 15. While the very last step of rolling is not in the drawings it is apparent that the procedure followed and shown in FIGS. 1 through 3 is continued until the glove pair 10 are completely rolled into a tightly contained compact package 14 with a width of "B" and a diameter of about one centimeter. This compact package 14 is attainable because the air within the unrolled glove pair 10 as shown in FIG. 1 is excluded from the rolled package 14. Although the glove pair 10 as rolled into the compact package 14 has no memory such that the glove pair 10 would unroll themselves the binding 25 is applied to hold the compact package 14 in a neat and orderly fashion. That is to say that handling of the rolled compact package 14 of the glove pair 10 is simplified by the binding 25 which holds the package together during the placement of the glove pair 10 in a product 26 (in FIG. 6) as will be explained. The preferred binding 25 is a piece of a pressure sensitive tape 27 used to hold the compact rolled cylindrical package of the present invention. The pressure sensitive tape 27 is wrapped around the compact package 14 at a middle 28 thereof relative to the width dimension "B" so as to circumscribe the roll and hold the package together. A tab 29 is formed by the tape ends 30 where they are brought together. The pressure sensitive qualities of the adhesive is selected to adhere well to adjacent tape 27 as in the tab 29, but so as not to stick to the rolled compact package 14 of the glove pair 10. Consequently, the tape 27 may be easily remove without damage to the glove pair 10.

FIG. 4 illustrates a compact package 14a of a glove pair 10a where an elastic band 31 commonly called a rubber band is applied to hold the compact package 14a together. The elastic band 31 is applied about the middle 28a of the of the compact package 14a at approximately the center of the width "B". Specifically, the elastic band 31 is circumferentially stretched, placed over in the preferred location and orientation and released. The restoring elastic force or memory of the elastic band 31 reduces the circumferential size of the elastic band 31 and thereby holds the compact package 14a. FIG. 4 also shows an alternate embodiment in that there is a innerwrap 32 rolled up into the compact package 14a of the glove pair 10a. The innerwrap 32 is placed between the glove pair 10a in order to separate the individual gloves 15a such that they do not interfere with each other such as by sticking. For example, if the particular gloves are manufactured without a donning powder there is a possibility that they may stick to each other after being rolled together into the compact package 14a. The innerwrap 32 may be a piece of paper, plastic or other suitable separating material which is not very thick, is flexible and has about the same dimensions as the glove pair 10a, i.e. width and length.

Figure 6:
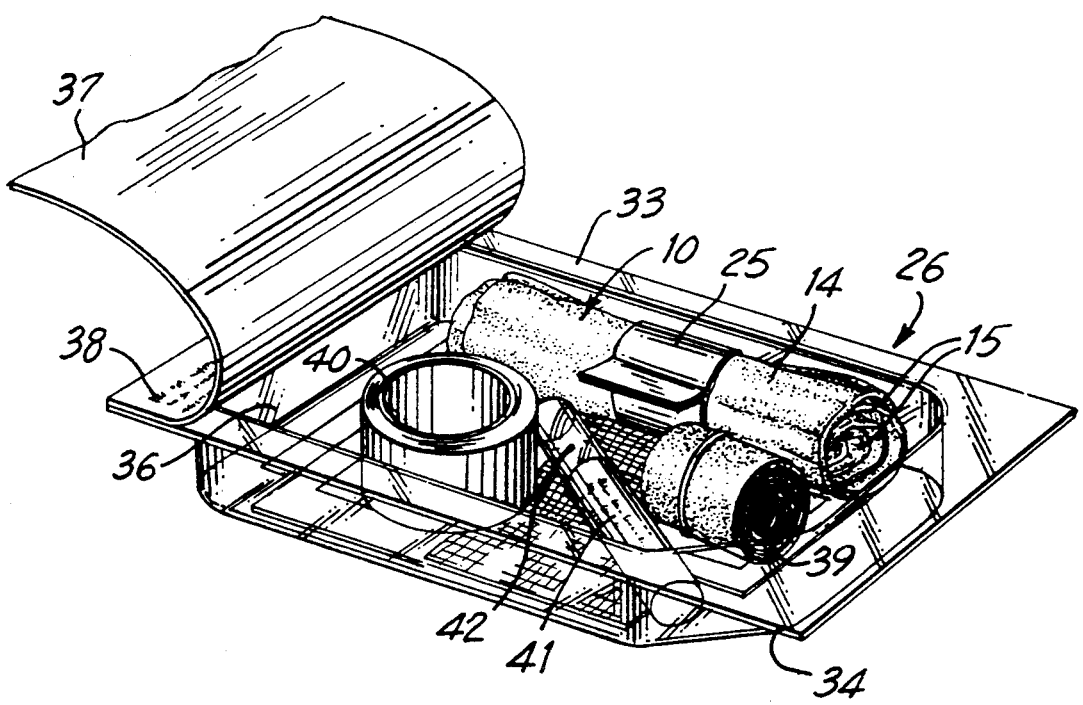
FIG. 6 is perspective view of a kit including components for a medical procedure with the preferred form of the binding of the compact rolled cylindrical package of the present invention with a pressure sensitive tape holding the rolled gloves.

FIG. 6 is perspective view of a kit 33 including components for a medical procedure with the compact rolled cylindrical package 14 of the present invention with the preferred form of a pressure sensitive tape 27 holding the rolled gloves 15. The kit includes a tray 34 formed of a sheet of transparent plastic. The tray 34 has a flange 35 and a recessed well 36 to form the component containing blister of the tray 34. The flange 35 is about the periphery of the recessed well 36 and is arranged to support a cover 37 in the form of a sheet of material which has indicia 38 facing outwardly to instruct the user as to the nature of the kit 33 and its source. The cover 37 is heat sealed or otherwise bonded to the flange 35 to create a barrier and provide sterility protection for the components in the recessed well 36. Although not shown completely sealed, the cover 37 is sealed across the entire well 36 and attached to the flange 35 all about the the tray 34 in its normal completely manufactured condition.

In the recessed well 36 of the tray 34 are various components for a medical procedure. The tray 34 is shown with the cover 37 peeled part way back to reveal typical components used in a catherization procedure. In particular, there is a tourniquet 39 shown as a tightly rolled strip of highly elastic rubber which may be tied around a patient's limb to restrict blood flow and make the vessels in the limb stand out. The tourniquet 39 is used in aiding the location of a blood vessel for purposes of inserting a catheter with an over the needle technique or other similar medical procedure. A dressing 40, including an adhesive member or an absorbent member is used in connection with the application of the catheter or other medical device to the blood vessel is also in the recessed well 36. An antimicrobial treatment 41 used to disinfect an area of skin before application of the medical device into the vessel is usually included in the kit 33 and is specifically shown as a breakable vial 42 in FIG. 6. The glove pair 10 formed into the rolled compact package 14 is placed to one side of the well 36 in the tray 34 the diametrical dimension of the gloves 15 is such the compact package 14 fits within the recessed well 36 under the cover 37.

The method for rolling a glove pair 10 into a relatively cylindrical package includes laying the glove pair 10 out in side by side juxtaposed relationwherein the finger ends 11 of the respective gloves 15 are adjacent to one another, the palm or back hand parts 12 of the respection gloves 15 are adjacent to one another, and the cuff portions 13 of the respective gloves 15 are juxtaposed to one another. The method includes the step of gathering the finger ends 11 of the adjacent gloves 15 into a relatively axial bundle with respect to the elongate longitudinal dimension of the adjacent glove pair 10. The further step of rolling the glove pair from the finger ends of the juxtaposed gloves 15 to the hand parts 12 against a relatively flat and rigid surface 21 in order to exclude any air within the gloves 15 by the pressure applied against the surface 21 while rolling, incorporating the thumbs 17 of the adjacent juxtaposed gloves 15 into the rolled bundle is accomplished. To complete the compact package 14 the method includes continuing to roll the gloves 15 along their elongate longitudinal dimension toward the cuff portions 13, while bearing against the bundle to continue to drive remaining air from the gloves 15 and out from the cuff portions 13 as the glove pair is rolled into the compact cylindrical package 14 about the width "B" of the gloves 15.

An additional step of holding the rolled gloves 15 with the binding 25 such as the elastic band 31 shaped member or a piece of pressure sensitive adhesive tape 27. An alternate method may include the steps of adding the piece of innerwrap 32 between the glove pair of juxtaposed gloves 15 and creating a sandwich for rolling into the cylindrical compact package 14.

The compact package 14 includes the glove pair 10 formed of a thin, flexible resilient material placed juxtaposed to one another. The glove pair 10 has the plurality of finger ends 11 against one another, the pair of hand parts 12 against one another and the pair of cuff portions 13 against one another. The glove pair 10 is rolled up together along its longitudinal elongate dimension from the finger ends 11 to the cuff portions 13, to drive air entrapped within the gloves 15 by the process of rolling from the finger ends 11 to the cuff portions 13. The compact package 14 presents the cuff portions 13 of each glove 15 at the periphery of the rolled generally cylindrical glove pair for ease in access to the inside of each glove 15 during donning. The binding 25 located about the middle 28 of the rolled glove pair 10 circumscribes the cylindrical compact package 14 formed thereby for holding the rolled glove pair 10 together.

The compact package 14 is such that the length of the unrolled glove pair 10 is substantially greater than the width "B" and the rolled glove pair 10 is diametrically less than the width "B" thereof.

Those skilled in the art understand that changes in materials, dimensions, physical relationships and the like may be made without departing from the scope of the inventions covered by the claims which follow.

What is claimed is:

1. A method for rolling a pair of nonporous film gloves into a generally cylindrical package comprising: laying out a pair of gloves in an arrangement on a generally flat and rigid surface, wherein each glove of said pair has a plurality of finger end portions, a hand portion and a cuff portion, said arrangement comprising placing said gloves one on top of the other so that said finger ends are adjacent each other, said hand portions are adjacent and said cuff portions are adjacent, said arrangement having a longitudinal axis from said finger ends to said cuff portion;

gathering said finger ends of said pair into a bundle generally aligned with said longitudinal axis;

forming a generally cylindrical package from said pair by rolling on said surface said gathered finger ends about an axis generally perpendicular to said longitudinal axis toward said hand portion and thence to said cuff portion, said rolling serving to substantially expel air entrapped by said pair;

and holding said generally cylindrical package with a packaging material.

2. The method of the claim 1 wherein said holding step comprises holding the rolled gloves with a binding.

3. The method of claim 2 with the additional step of using an elastic band shaped member for binding.

4. The method of claim 3 with the additional steps of expanding the band shaped member to fit over the rolled gloves and releasing the band shaped member to retain the rolled gloves in the cylindrical roll.

5. The method of claim 2 wherein the step of binding is accomplished by using a piece of pressure sensitive adhesive tape.

6. The method of claim 1 with the additional steps of adding a piece of innerwrap between the gloves of the pair of gloves and creating a sandwich for rolling into the cylindrical package.

7. The method of the claim 6 wherein said holding step comprises holding the rolled gloves with a binding.

8. The method of claim 7 wherein the step of binding is accomplished by using an elastic band shaped member.

9. The method of claim 8 with the additional steps of expanding the band shaped member to fit over the rolled gloves and releasing the band shaped member to retain the rolled gloves in the cylindrical roll.

10. The method of claim 7 wherein the step of binding is accomplished by using a piece of pressure sensitive adhesive tape.

* * * * *